US010477079B2

(12) United States Patent
Mueckl et al.

(10) Patent No.: US 10,477,079 B2
(45) Date of Patent: *Nov. 12, 2019

(54) VISUAL INSPECTION DEVICE

(71) Applicant: Milwaukee Electric Tool Corporation, Brookfield, WI (US)

(72) Inventors: Gareth Mueckl, Milwaukee, WI (US); Jason R. Crowe, Wauwatosa, WI (US); Benjamin Oliver Ryan Cabot, Milwaukee, WI (US)

(73) Assignee: MILWAUKEE ELECTRIC TOOL CORPORATION, Brookfield, WI (US)

( * ) Notice: Subject to any disclaimer, the term of this patent is extended or adjusted under 35 U.S.C. 154(b) by 43 days.

This patent is subject to a terminal disclaimer.

(21) Appl. No.: 15/642,611

(22) Filed: Jul. 6, 2017

(65) Prior Publication Data

US 2017/0310858 A1    Oct. 26, 2017

Related U.S. Application Data

(63) Continuation of application No. 14/057,694, filed on Oct. 18, 2013, now Pat. No. 9,736,342.
(Continued)

(51) Int. Cl.
*H04N 5/225* (2006.01)
*G02B 23/24* (2006.01)
(Continued)

(52) U.S. Cl.
CPC ....... *H04N 5/2252* (2013.01); *A61B 1/00052* (2013.01); *A61B 1/0052* (2013.01);
(Continued)

(58) Field of Classification Search
None
See application file for complete search history.

(56) References Cited

U.S. PATENT DOCUMENTS 4,722,337 A * 2/1988 Losch ............... A61B 18/20
219/121.61
4,963,903 A 10/1990 Cane
(Continued)

FOREIGN PATENT DOCUMENTS

CN  201497709 U  6/2010
CN  202364288 U  8/2012
(Continued)

OTHER PUBLICATIONS

DeWalt, Instruction Manual DCT410, DCT411, DCT412 12V Max* Cordless Inspection Camera (2010) Part No. 133375, 64 pages.
(Continued)

*Primary Examiner* — Heather R Jones
(74) *Attorney, Agent, or Firm* — Michael Best & Friedrich LLP (57) ABSTRACT

A visual inspection device includes a housing, a handle coupled to the housing that is grasped by a user while the device is in use, and an articulating camera unit coupled to the housing. The articulating camera unit includes a flexible cable with a first end coupled to the housing and a second end, a camera coupled to the second end of the flexible cable and operable to transmit image data through the flexible cable, and an articulation mechanism operable to articulate the camera relative to the flexible cable. The articulation mechanism includes a mount that is removably coupled to the housing. The articulating camera unit further includes a means for securing the mount to the housing in a plurality of different orientations relative to the housing. The visual inspection device further includes a display unit coupled to the housing to display an image transmitted by the articulating camera unit.

18 Claims, 9 Drawing Sheets

Related U.S. Application Data (60) Provisional application No. 61/829,002, filed on May 30, 2013, provisional application No. 61/716,153, filed on Oct. 19, 2012.

(51) Int. Cl.
  *A61B 1/00* (2006.01)
  *A61B 1/005* (2006.01)

(52) U.S. Cl.
  CPC ........ *A61B 1/0057* (2013.01); *A61B 1/00105* (2013.01); *G02B 23/2476* (2013.01)

(56) References Cited

U.S. PATENT DOCUMENTS

| | | |
|---|---|---|
| 5,938,678 A * | 8/1999 | Zirps ............... A61B 17/29 606/167 |
| 5,956,077 A | 9/1999 | Qureshi |
| 6,030,339 A | 2/2000 | Tatsuno |
| 6,056,450 A | 5/2000 | Walling |
| 6,057,608 A | 5/2000 | Bailey, Jr. |
| 6,091,453 A | 7/2000 | Coan |
| 6,197,017 B1 | 3/2001 | Brock |
| 6,221,007 B1 | 4/2001 | Green |
| 6,313,869 B1 | 11/2001 | Hyp |
| 6,369,849 B1 | 4/2002 | Rzyski |
| 6,398,549 B1 | 6/2002 | Koivisto |
| 6,411,332 B1 | 6/2002 | Whitby |
| 6,419,626 B1 | 7/2002 | Yoon |
| 6,432,046 B1 | 8/2002 | Yarush |
| 6,450,706 B1 | 9/2002 | Chapman |
| 6,517,207 B2 | 2/2003 | Chapman |
| 6,673,012 B2 | 1/2004 | Fujii |
| 6,809,759 B1 | 10/2004 | Chiang |
| 6,847,394 B1 | 1/2005 | Hansen |
| 6,855,107 B2 | 2/2005 | Avni |
| 6,856,353 B1 | 2/2005 | Misawa |
| 6,923,542 B2 | 8/2005 | Harris |
| 6,927,332 B1 | 8/2005 | Phillips |
| 6,960,161 B2 | 11/2005 | Amling et al. |
| 6,987,787 B1 | 1/2006 | Mick |
| 7,008,375 B2 | 3/2006 | Weisel |
| 7,030,904 B2 | 4/2006 | Adair |
| 7,037,006 B2 | 5/2006 | Chapman |
| 7,048,453 B1 | 5/2006 | Gaunt |
| 7,121,745 B2 | 10/2006 | Chapman |
| 7,214,183 B2 * | 5/2007 | Miyake ............... A61B 1/00039 600/104 |
| 7,217,044 B1 | 5/2007 | Marks, Jr. |
| 7,283,155 B1 | 10/2007 | Marks, Jr. |
| 7,304,618 B2 | 12/2007 | Plathe |
| 7,316,646 B2 | 1/2008 | Amling |
| 7,384,308 B2 | 6/2008 | Boehnlein |
| 7,431,619 B2 | 10/2008 | Boehnlein et al. |
| 7,528,609 B2 | 5/2009 | Savicki, Jr. |
| 7,551,197 B2 | 6/2009 | Penza |
| 7,553,275 B2 | 6/2009 | Padget |
| 7,581,988 B2 | 9/2009 | Boehnlein et al. |
| 7,584,534 B2 | 9/2009 | Pease |
| 7,670,284 B2 | 3/2010 | Padget |
| 7,758,495 B2 | 7/2010 | Pease |
| 7,927,027 B2 | 4/2011 | Yamakose |
| 7,929,050 B2 | 4/2011 | Liang |
| 7,929,846 B2 | 4/2011 | Sukenari |
| 7,979,689 B2 | 7/2011 | Watt |
| 7,990,102 B2 | 8/2011 | Scheucher |
| 8,002,480 B2 | 8/2011 | Polster |
| 8,128,558 B2 | 3/2012 | Amling |
| 8,189,042 B2 | 5/2012 | Mandrachia |
| 8,189,043 B2 | 5/2012 | Schneider |
| 8,199,251 B2 | 6/2012 | Woodman |
| 8,218,074 B2 | 7/2012 | Pease |
| 8,251,157 B2 | 8/2012 | Gray |
| 8,269,828 B2 | 9/2012 | Miller |
| 8,269,829 B2 | 9/2012 | Miller |
| 8,279,278 B2 | 10/2012 | Park |
| 8,382,742 B2 | 2/2013 | Hermann |
| 8,453,639 B2 | 6/2013 | Kim |
| 8,558,882 B1 | 10/2013 | Kotab |
| 8,633,980 B2 | 1/2014 | Liu |
| 2001/0037509 A1 | 11/2001 | Kligman |
| 2002/0097321 A1 | 7/2002 | McBride |
| 2003/0035048 A1 | 2/2003 | Shipp |
| 2003/0137310 A1 | 7/2003 | Holzel |
| 2004/0036791 A1 | 2/2004 | Voss |
| 2005/0018042 A1 | 1/2005 | Rovegno |
| 2005/0024495 A1 | 2/2005 | Hamrelius |
| 2005/0122416 A1 | 6/2005 | Ryu |
| 2005/0129108 A1 | 6/2005 | Bendall |
| 2005/0143626 A1 | 6/2005 | Prescott |
| 2005/0289631 A1 | 12/2005 | Shoemake |
| 2006/0061663 A1 | 3/2006 | Park |
| 2006/0139459 A1 | 6/2006 | Zhong |
| 2006/0155168 A1 | 7/2006 | Pease |
| 2006/0167340 A1 | 7/2006 | Pease |
| 2006/0203998 A1 | 9/2006 | Ben-Arie |
| 2006/0249678 A1 | 11/2006 | Wu |
| 2006/0281972 A1 | 12/2006 | Pease |
| 2007/0173697 A1 | 7/2007 | Dutcher |
| 2007/0185379 A1 | 8/2007 | Newman |
| 2007/0213595 A1 * | 9/2007 | Ravikumar ........ A61B 17/0218 600/217 |
| 2007/0225556 A1 | 9/2007 | Ortiz |
| 2008/0026647 A1 | 1/2008 | Boehnlein et al. |
| 2008/0058598 A1 | 3/2008 | Ries |
| 2009/0003822 A1 | 1/2009 | Tyner |
| 2009/0163929 A1 * | 6/2009 | Yeung ................ B25J 9/047 606/130 |
| 2009/0196459 A1 | 8/2009 | Watt |
| 2009/0225159 A1 | 9/2009 | Schneider |
| 2009/0229842 A1 | 9/2009 | Gray |
| 2009/0309967 A1 | 12/2009 | Kim |
| 2010/0033563 A1 | 2/2010 | Boehnlein et al. |
| 2010/0033986 A1 | 2/2010 | Schober |
| 2010/0087708 A1 | 4/2010 | Chen |
| 2010/0101569 A1 | 4/2010 | Kim |
| 2010/0145146 A1 | 6/2010 | Melder |
| 2010/0160736 A1 | 6/2010 | Padget |
| 2010/0181990 A1 | 7/2010 | Hudson |
| 2010/0208056 A1 | 8/2010 | Olsson |
| 2011/0090331 A1 | 4/2011 | Draper |
| 2011/0090493 A1 | 4/2011 | Schober |
| 2011/0130627 A1 | 6/2011 | McGrail |
| 2011/0130632 A1 | 6/2011 | McGrail |
| 2011/0221907 A1 | 9/2011 | Smart |
| 2011/0273556 A1 | 11/2011 | Lyons |
| 2011/0317064 A1 | 12/2011 | Watts |
| 2012/0008042 A1 | 1/2012 | Wang |
| 2012/0016197 A1 | 1/2012 | Turnbull |
| 2012/0162401 A1 | 6/2012 | Melder |
| 2012/0236138 A1 | 9/2012 | Liu |

FOREIGN PATENT DOCUMENTS

| | | |
|---|---|---|
| GB | 916616 A | 1/1963 |
| JP | 2006319401 A | 11/2006 |
| WO | WO-9738526 A1 | 10/1997 |
| WO | WO-2006071948 A2 | 7/2006 |
| WO | WO-2007015101 A2 | 2/2007 |

OTHER PUBLICATIONS

DialogWeb, "Wireless Borescopes capture images and video in small spaces" <http:dialogweb.comcgidwclient?req=1352746359563> website available as early as Dec. 14, 2009.

European Search Report for Application No. 11170911 dated Oct. 28, 2011 (1 page).

Extech Instruments, Product Sheet Model HDV-TX1 (2013) HDV-TX1-EU-EN V2.3 Mar. 2013, 2 pages.

Extech Instruments, User Guide—High Definition VideoScope Model HDV600 (2012) HDV600-EU-EN-V2.7 Oct. 2012, 11 pages.

(56) References Cited

OTHER PUBLICATIONS

Extech Instruments, User's Guide Video Borescope—Models BR200 and BR250 (2009) BR200-BR250 V4.3 Aug. 2009, 11 pages.
Extech Instruments, User's Guide—Video Borescope Model BR200 (2009) BR200 V3.0, 12 pages.
Extech Instruments, Video BorescopeWireless Inspection Camera (2010) 1 page.
Extech, "Introducing the New BR200 Inspection Camera and Video Borescope" <http:www.youtube.comwatch?v=2iJIEy3iSHs> webpage available as early as Jul. 1, 2009.
Fluke, "Fluke 233 Remote Display Multimeter" <http:www.fluke.comflukeusendigital-multimetersfluke-233.htm?PID-=56054> website accessed on Oct. 26, 2012.
Fluke, 233 True-rms Remote Display Digital Multimeter Users Manual (Sep. 2009) 54 pages.
General Tools & Instruments, DCS200DCS300 User's Manual (2009) MAN#DCS200DCS300 Jul. 2009, 16 pages.
International Search Report and Written Opinion for Application No. PCTUS2013065667 dated Jan. 16, 2014 (12 pages).
PRWeb Online Visibility Inspection Camera Wins NECA Showstopper Award <http:www.prweb.comreleasesextech-inspectioncamera-borescopeprwe- b3239094.htm> website available as early as Nov. 21, 2009.
Security InfoWatch, "SecurityMan Introduces ToolCam" <http:www.securityinfowatch.compress.sub.--release10489753securit- yman-introduces-toolcam> webpage available as early as Aug. 14, 2009.
SecurityMan, Inc., ToolCam Cordless Inspection Camera with Wireless Detachable Monitor, publicly available as early as Jul. 9, 2009 (2 pages).
SecurityMan, Inc., ToolCam II Cordless Inspection 9.5mm Camera with Wireless Detachable Monitor, publicly available as early as Jul. 9, 2009 (2 pages).
SecurityMan, Inc., ToolCam User Manual Cordless Inspection Camera with Wireless Detachable Monitor (2009) 24 pages.

\* cited by examiner

VISUAL INSPECTION DEVICE

CROSS-REFERENCE TO RELATED APPLICATIONS

This application is a continuation of co-pending U.S. patent application Ser. No. 14/057,694 filed on Oct. 18, 2013, which claims the benefit of U.S. Provisional Patent Application No. 61/716,153 filed on Oct. 19, 2012 and U.S. Provisional Patent Application No. 61/829,002 filed on May 30, 2013, the entire contents of which are incorporated herein by reference.

FIELD OF THE INVENTION

The present invention relates to a visual inspection device and, more particularly, to a hand-held visual inspection device for viewing confined or otherwise difficult to access locations.

BACKGROUND OF THE INVENTION

Visual inspection devices (e.g., borescopes, endoscopes, or the like) provide tradespeople, such as plumbers, electricians, mechanics, HVAC (heating, ventilation, and air conditioning) professionals, welders, carpenters, MRO (maintenance, repair, and operations) professionals, or the like, with means to view locations that are inaccessible without dismantling or removing surrounding structures. For example, visual inspection devices are used to inspect inside pipes, walls, floors, aircraft or automobile engines, or other equipment that include narrow, small, and/or dark passageways.

SUMMARY OF THE INVENTION

The invention provides, in one aspect, a visual inspection device including a housing, a handle coupled to the housing that is grasped by a user while the device is in use, and an articulating camera unit coupled to the housing. The articulating camera unit includes a flexible cable with a first end coupled to the housing and a second end, a camera coupled to the second end of the flexible cable and operable to transmit image data through the flexible cable, and an articulation mechanism operable to articulate the camera relative to the flexible cable. The articulation mechanism includes a mount that is removably coupled to the housing. The articulating camera unit further includes a means for securing the mount to the housing in a plurality of different orientations relative to the housing. The visual inspection device further includes a display unit coupled to the housing to display an image transmitted by the articulating camera unit.

Other features and aspects of the invention will become apparent by consideration of the following detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

DETAILED DESCRIPTION

Figure 1:
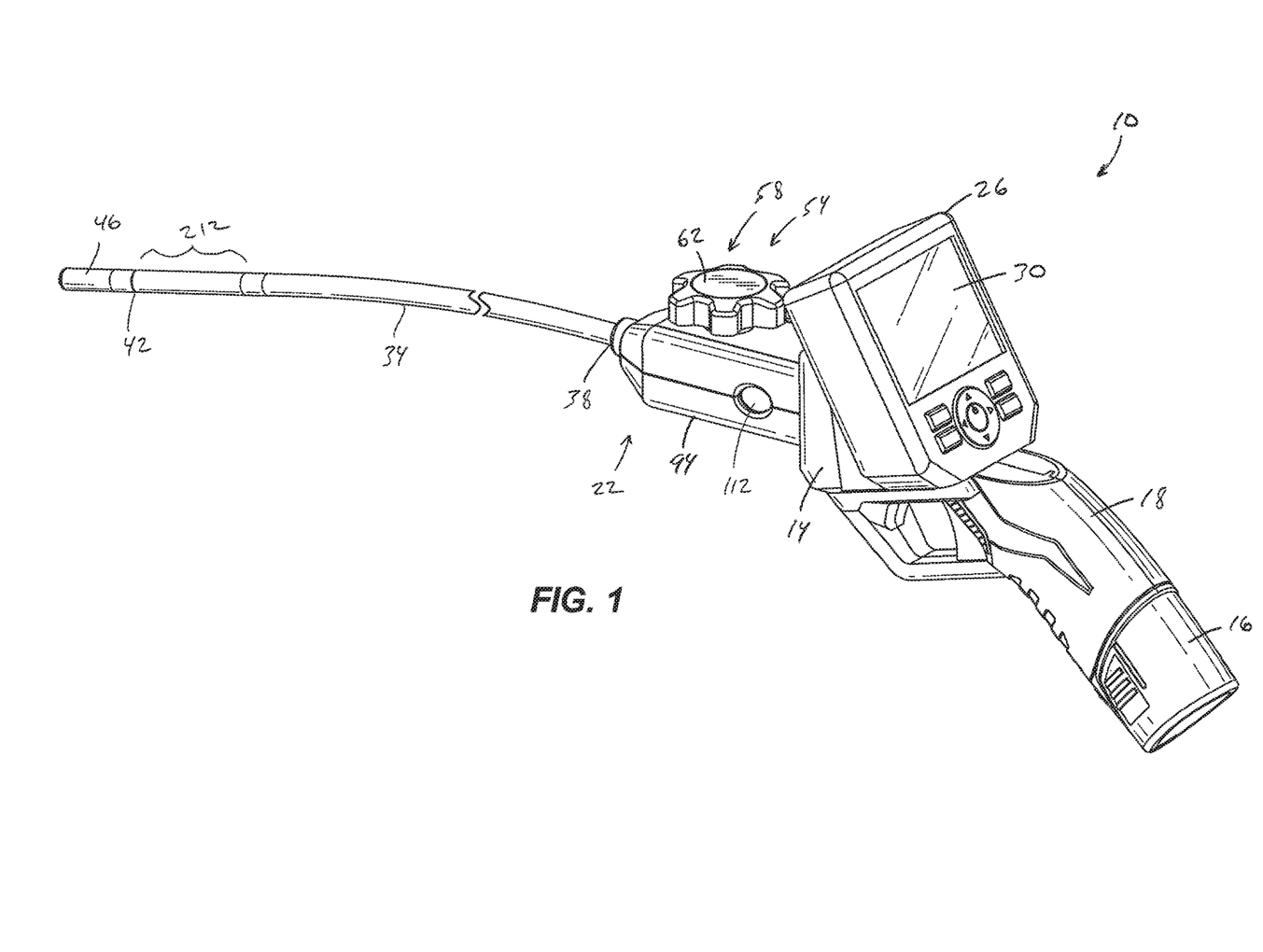
FIG. 1 is a front perspective view of a visual inspection device of the invention.

FIG. 1 illustrates a visual inspection device 10 configured as a hand-held unit for a user (e.g., a plumber, an electrician, a mechanic, an HVAC professional, a welder, a carpenter, an MRO professional, or the like) to view the interior of a confined space (e.g., a pipe, a wall, a floor, an engine, or the like). The visual inspection device 10 includes a housing 14 and a handle 18 extending from the housing 14 that is grasped by a user while the device is in use. The visual inspection device 10 also includes a battery pack 16 supported by the handle 18 for powering the device. Particularly, the handle 18 includes a cavity (not shown) in which the battery pack 16 is removably received. Such a battery pack 16 may be configured as a rechargeable power tool battery pack 16 that is usable with a variety of power tools (e.g., drills, screwdrivers, saws, or the like). The battery pack 16 may be a twelve-volt (12V) battery pack. The battery pack 16 may also include three battery cells having, for example, a lithium (Li), lithium-ion (Li-ion), or other lithium-based chemistry. For example, the battery cells may have a chemistry of lithium-cobalt (Li—Co), lithium-manganese (Li—Mn) spinel, or Li—Mn nickel. In such embodiments, each battery cell may have a nominal voltage of about, for example, 3.6V, 4.0V, or 4.2V. In other embodiments, the battery cells may have a nickel-cadmium, nickel-metal hydride, or lead acid battery chemistry. In further embodiments, the battery pack 16 may include fewer or more battery cells, and/or each battery cell may have a different nominal voltage.

The visual inspection device 10 further includes an articulating camera unit 22 coupled to the housing 14 and a display unit 26 having a screen 30 for displaying an image transmitted by the articulating camera unit 22. With continued reference to FIG. 1, the articulating camera unit 22 includes a flexible cable 34 having a first or proximal end 38 coupled to the housing 14 and a second or distal end 42. The articulating camera unit 22 further includes a camera 46 coupled to the distal end 42 of the flexible cable 34. The camera 46 transmits image data through the flexible cable 34, though other forms of data may also be transmitted through the flexible cable 34 (e.g., sound, etc.). Such a camera is described and shown in U.S. Pat. No. 8,189,043, the entire content of which is incorporated herein by reference.

Figure 2:
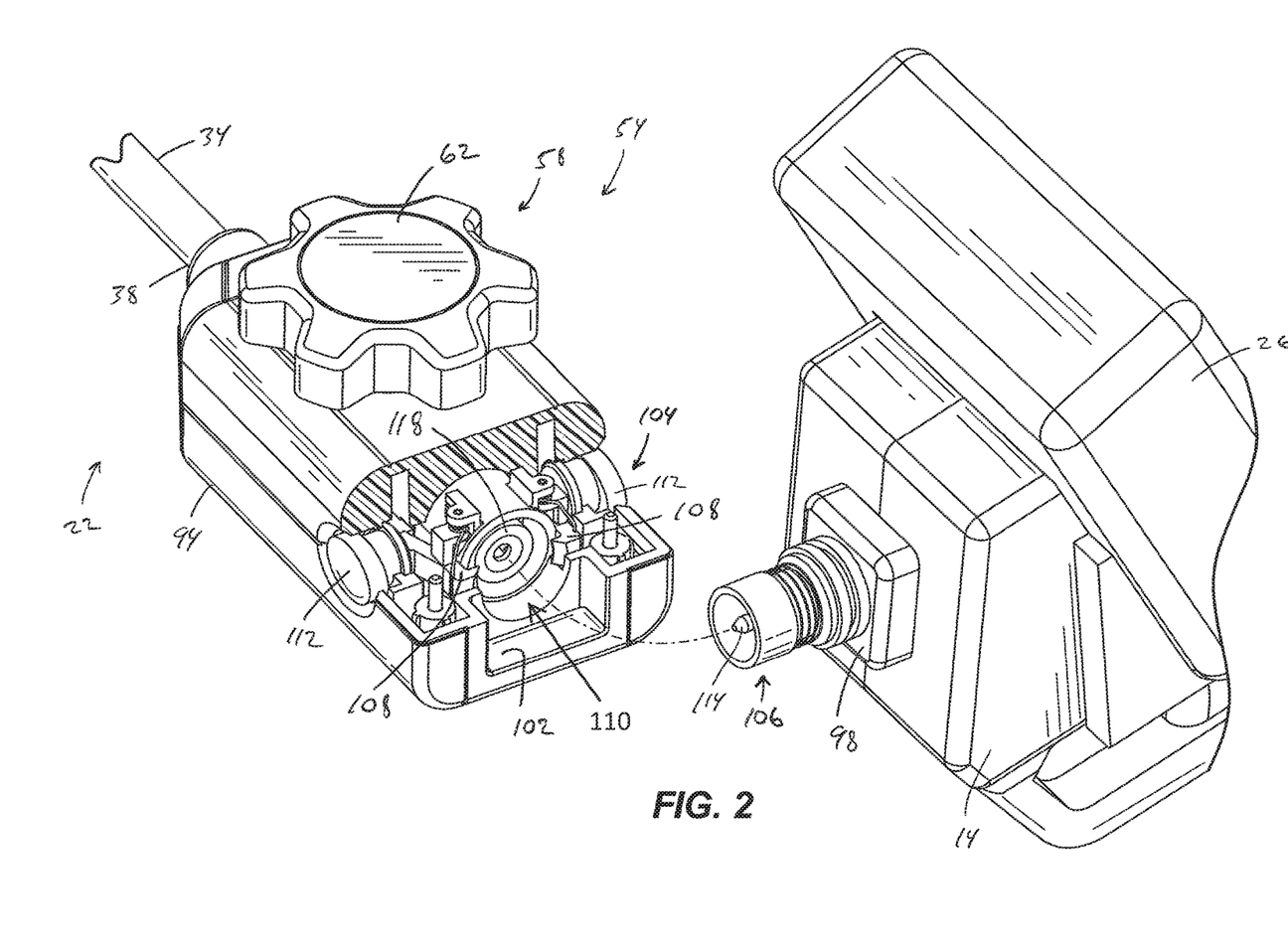
FIG. 2 is a partial cutaway view of an articulating camera unit exploded from a housing of the visual inspection device of FIG. 1.
Figure 6:
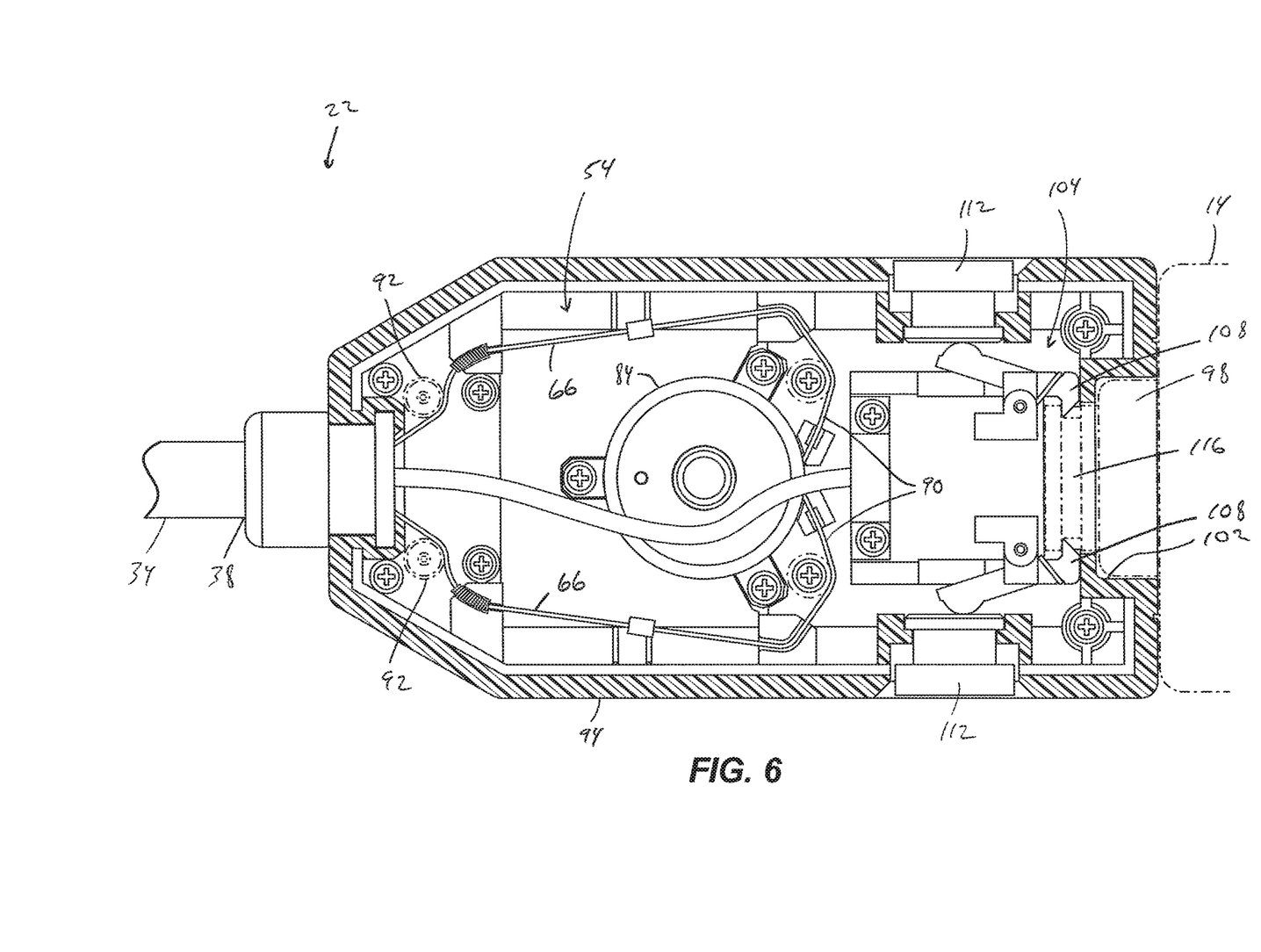
FIG. 6 is a cross-sectional view of a portion of the articulating camera unit installed to the housing of the visual inspection device.

With reference to FIGS. 1, 2, and 6, the articulating camera unit 22 also includes an articulation mechanism 54 for articulating and maneuvering the camera 46 relative to the flexible cable 34. The articulation mechanism 54 includes an actuator 58 (FIGS. 1 and 2) that is manipulatable by a user of the visual inspection device 10 to articulate the camera 46 relative to the flexible cable 34. In the illustrated embodiment of the device as shown in FIGS. 1 and 2, the actuator 58 is a dial 62 that is rotatable in a first direction (e.g., counter-clockwise) for articulating the camera 46 in a first direction (e.g., left) relative to the flexible cable 34. Likewise, the dial 62 is rotatable in a second direction (e.g., clockwise) for articulating the camera 46 in a second direction (e.g., right) relative to the flexible cable 34. As such, the user of the visual inspection device 10 may selectively articulate or maneuver the camera 46 in a certain direction by rotating the dial 62. Alternatively, the actuator 58 may be configured differently to provide an alternative user interface (e.g. a slider, a lever, etc.).

Figure 7:
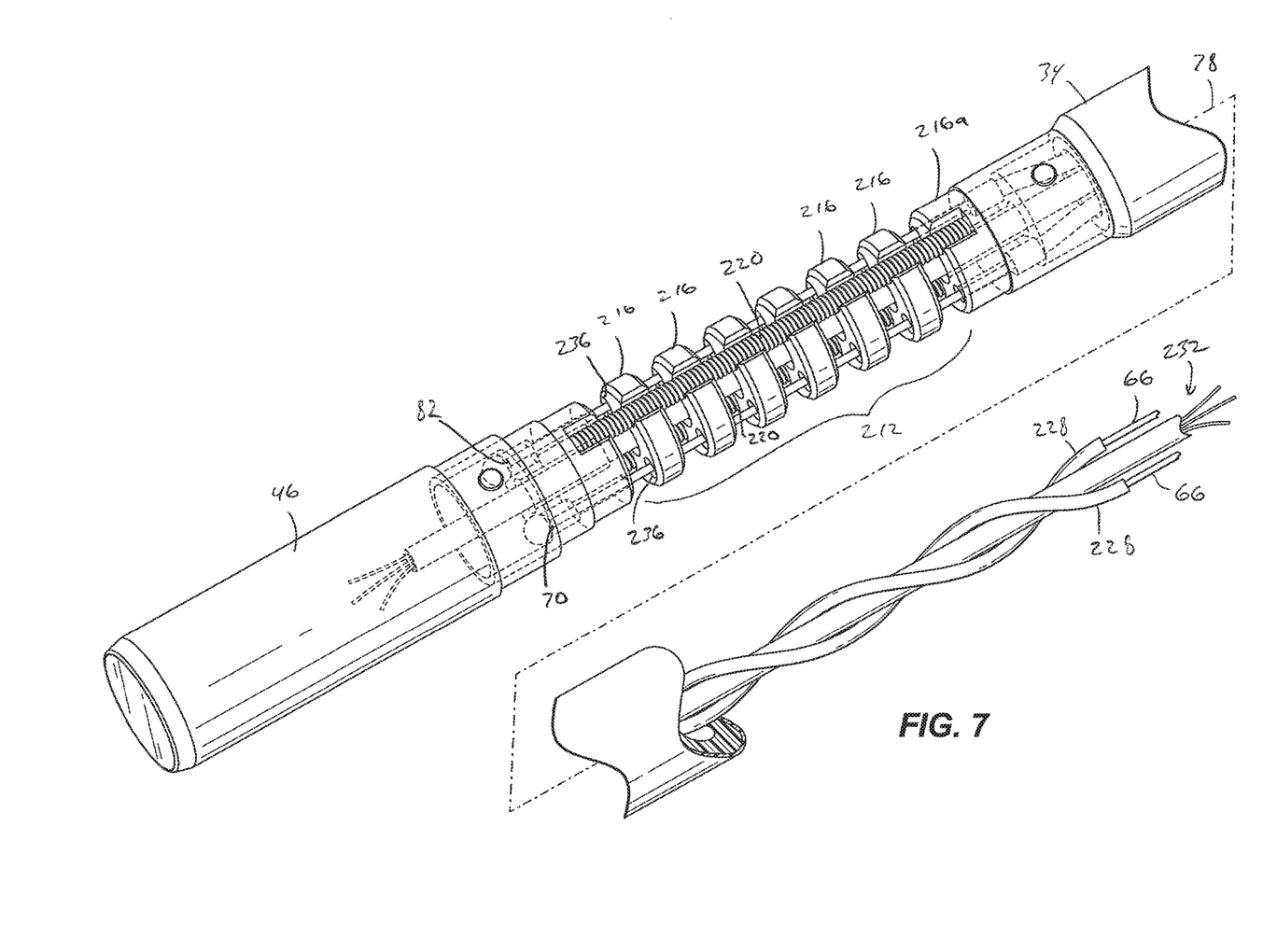
FIG. 7 is a perspective view of an articulating section of a flexible cable of the articulating camera unit, illustrating a camera oriented coaxially with the articulating section.

With reference to FIGS. 6 and 7, the articulating mechanism 54 also includes a continuous wire 66 disposed within and routed through the flexible cable 34. A first end 70 of the wire 66 is attached to the camera 46 at a first location radially offset from a longitudinal axis 78 of the camera 46, while a second end 82 of the wire 66 is attached to the camera 46 at a second location radially offset from the longitudinal axis 78 of the camera 46 (FIG. 7). In the illustrated embodiment of the visual inspection device 10, the first and second ends 70, 82 of the wire 66 are attached to the camera 46 on opposite sides of the longitudinal axis 78. Alternatively, the ends of the wire 70, 82 may be attached to the camera 46 at other locations.

Figure 8:
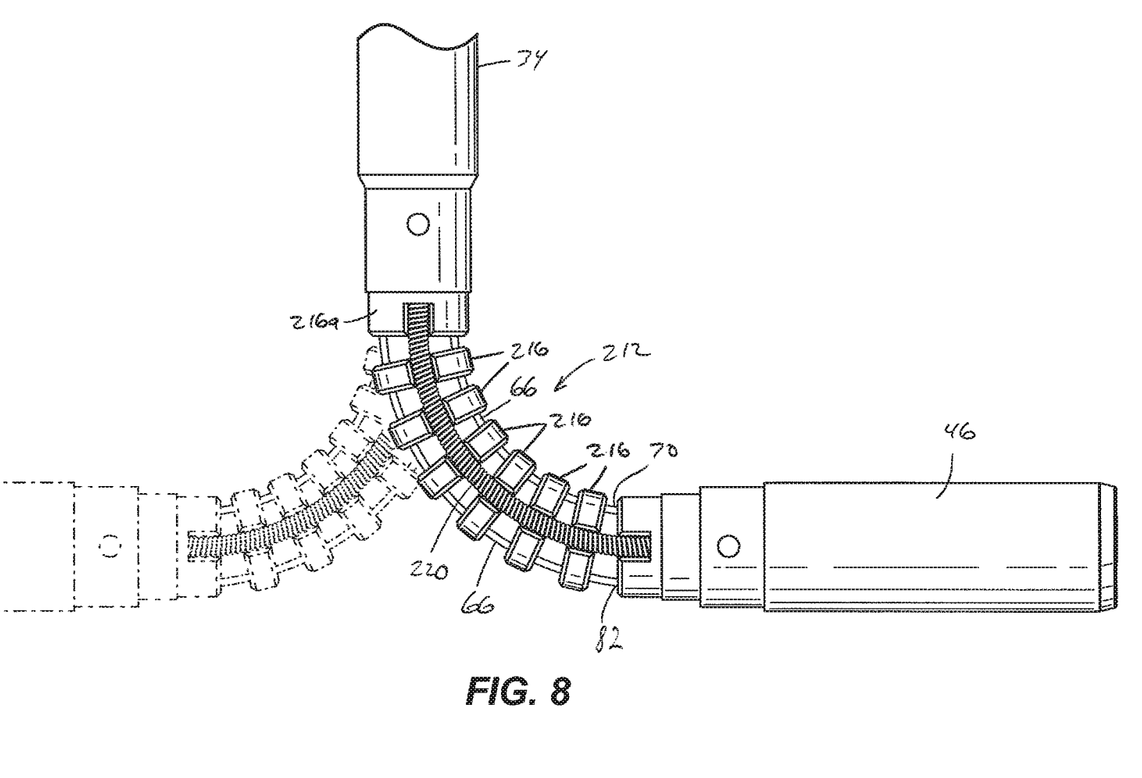
FIG. 8 is a plan view of the articulating section and camera of FIG. 7, illustrating the camera oriented transversely to the remainder of the flexible cable.

A middle portion 90 of the wire 66 is wrapped around a pulley 84 which, in turn, is coupled for co-rotation with the dial 62 such that tension may be developed in the wire 66 proximate one of the first and second ends 70, 82 in response to rotation of the dial 62 (FIG. 6). Moreover, rotation of the dial 62 in a first direction (e.g., counter-clockwise) develops tension in the wire 66 proximate the first end 70, and rotation of the dial 62 in a second direction (e.g., clockwise) develops tension in the wire 66 proximate the second end 82. As such, the user may rotate the dial 62 to turn the camera 46 to the left or right as shown in FIG. 8 to obtain an additional degree of freedom of movement for the camera 46. Alternatively, individual or separate wires may be utilized rather than the single continuous wire 66 wrapped around the pulley 84. The articulation mechanism 22 may further include two additional pulleys 92 (FIG. 6) in contact with respective lengths of the continuous wire 66 to reduce friction on the wire 66 as it is redirected into the flexible cable 34 and toward the camera 46.

Figure 3:
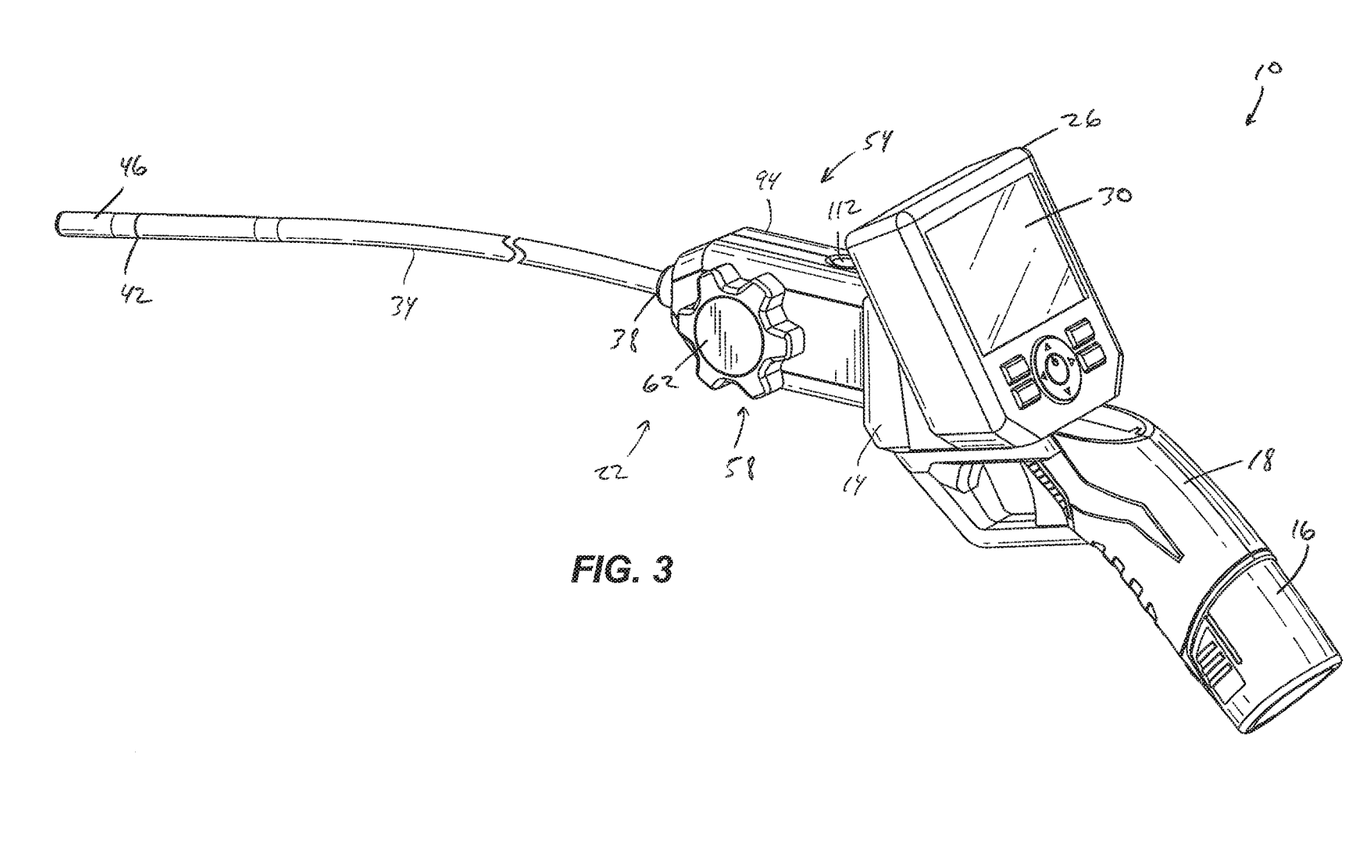
FIG. 3 is a front perspective view of the visual inspection device with the articulating camera unit installed in an alternate orientation.

With reference to FIGS. 1-3, the articulating camera unit 22 includes a mount 94 upon which the dial 62 is rotatably coupled. The mount 94, in turn, is removably coupled to the housing 14 in multiple orientations (FIGS. 1 and 3) to allow a user of the visual inspection device 10 to orient the dial 62 in a position that is either more comfortable or accessible for the user. In the illustrated embodiment of the device 10 as shown in FIG. 2, the housing 14 includes a boss 98 having a square cross-sectional shape, and the mount 94 includes a receptacle 102 having a corresponding square cross-sectional shape in which the boss 98 is received. Alternatively, the boss 98 and the receptacle 102 may be configured having any of a number of different non-circular cross-sectional shapes to inhibit relative rotation between the mount 94 and the housing 14.

With reference to FIG. 2, the mount 94 includes a detent or quick-release latch mechanism 104 for positively securing the mount 94 to the housing 14 in each of the different orientations shown in FIGS. 1 and 3. In the illustrated embodiment, the latch mechanism 104 includes pivotable arms 108 and corresponding buttons 112 for actuating the arms 108 between a spring-biased, radially inward position (shown in FIG. 2) and a radially outward position. As shown in FIG. 6, distal ends of the arms 108 are received within an annular groove 116 of an electrical connector 106, described in more detail below, for securing the mount 94 to the housing 14 in each of the different orientations shown in FIGS. 1 and 3. The detent or quick-release latch mechanism 104 allows the user of the visual inspection device 10 to quickly attach the articulating camera unit 22 to the housing 14 and remove the articulating camera unit 22 from the housing 14. Alternatively, the quick-release latch mechanism 104 may be omitted, and a snug fit may be employed between the boss 98 and the receptacle 102 for retaining the mount 94 to the housing 14.

With reference to FIG. 2, the visual inspection device 10 includes an electrical connector 106 extending from the housing 14, and the articulating camera unit 22 includes a mating electrical connector 110 within the mount 94. In the illustrated embodiment of the device 10, the electrical connector 106 is a multi-conductor cylindrical jack 114 and the electrical connector 110 is a corresponding cylindrical socket 118 located adjacent the receptacle 102 of the mount 94. Particularly, the electrical connector 106 is a four-conductor jack with an insulator (not shown) surrounding the jack 114, and the electrical connector 110 is a mating four-conductor socket 118. Such an electrical connector 106 is otherwise known as a Tip Ring Ring Sleeve (TRRS) connector. Alternatively, the electrical connectors 106, 110 may be configured in different ways, and may employ any of a number of different conductors depending upon the number of signals or channels of data that must be transmitted by the camera 46.

The cylindrical configuration of the jack 114 and the corresponding socket 118 enables the articulating camera unit 22 to be mounted to the housing 14 in multiple orientations to position the dial 62 in accordance with the user's comfort or ease of accessibility. Although the articulating camera unit 22 is capable of being mounted to the housing 14 in four different orientations corresponding to the square cross-sectional shape of the boss 98 and the mount receptacle 102 (FIG. 2), the boss 98 and the mount receptacle 102 may be configured in any of a number of non-circular cross-sectional shapes to permit more mounting orientations of the articulating camera unit 22 to accommodate additional placements of the dial 62 relative to the housing 14. As shown in FIG. 2, the electrical connector 106 extends from a rear side of the housing 14 but it is not limited to that location.

Figure 4:
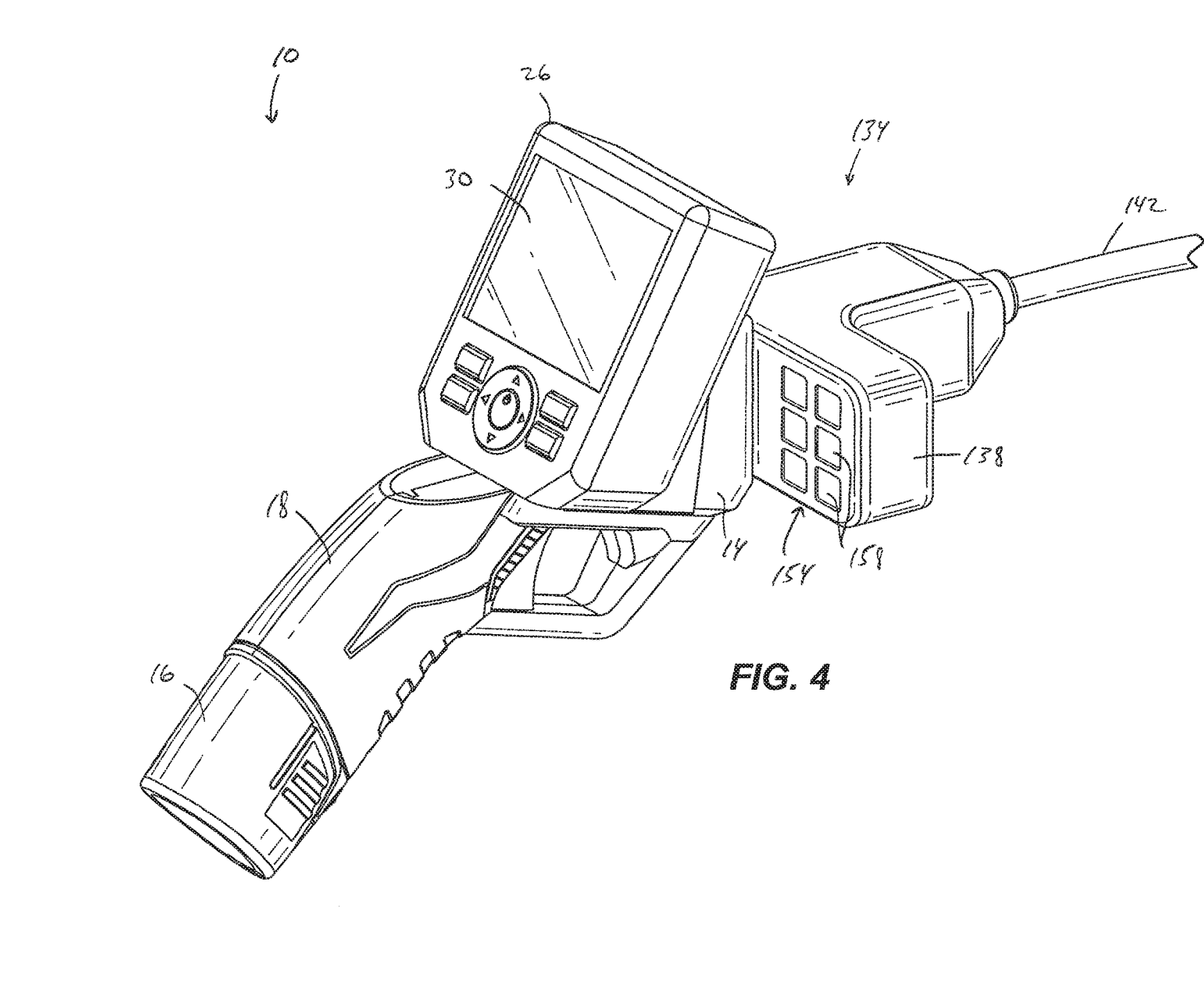
FIG. 4 is a front perspective view of the visual inspection device of FIG. 1 with a thermal imaging unit installed rather than the articulating camera unit.

With reference to FIG. 4, a thermal imager unit 134 may be coupled to the electrical connector 106 and interchangeable with the articulating camera unit 22. The thermal imager unit 134 includes a thermal camera (not shown), an interface module 138, and a flexible cable 142 interconnecting the thermal camera and the module 138. Like the mount 94 of the articulating camera unit 22, the interface module 138 includes a receptacle (not shown) having a square cross-sectional shape and an electrical connector (e.g., a TRRS-style electrical socket, not shown) accessible through the receptacle that is electrically connectable to the electrical connector 106 on the housing 14. As such, the interface module 138 may be supported upon the housing 14 in four different orientations, one of which is shown in FIG. 4. The module 138 may also include a similar detent mechanism or quick-release latch mechanism as that used in the articulating camera unit 22 so the module 138 may be secured to the boss 98 on the housing 14 in a similar manner. The module 138 includes a user interface 154 including buttons 158 for selecting options associated with the thermal imager unit 134 (e.g. temperature range, color schemes, etc.).

An adapter (not shown) may be coupled to the electrical connector 106 and interchangeable with either of the articulating camera unit 22 or the thermal imager unit 134 for using the visual inspection device 10 with a conventional sewer camera reel (not shown). Such a sewer camera reel includes a reel having an extended length (e.g., upwards of 200 feet) of flexible cable and a camera attached to a distal end of the flexible cable. The adapter includes a mount similar to the mount 94 of the articulating camera unit 22, an electrical connector (not shown) of a particular style for connection to the sewer camera reel, and an electrical cable interconnecting the electrical connector and the mount. Like the articulating camera unit 22, the adapter includes an electrical connector (e.g., a TRRS-style electrical socket) within the mount for connecting to the electrical connector 106 on the housing 14.

Figure 5:
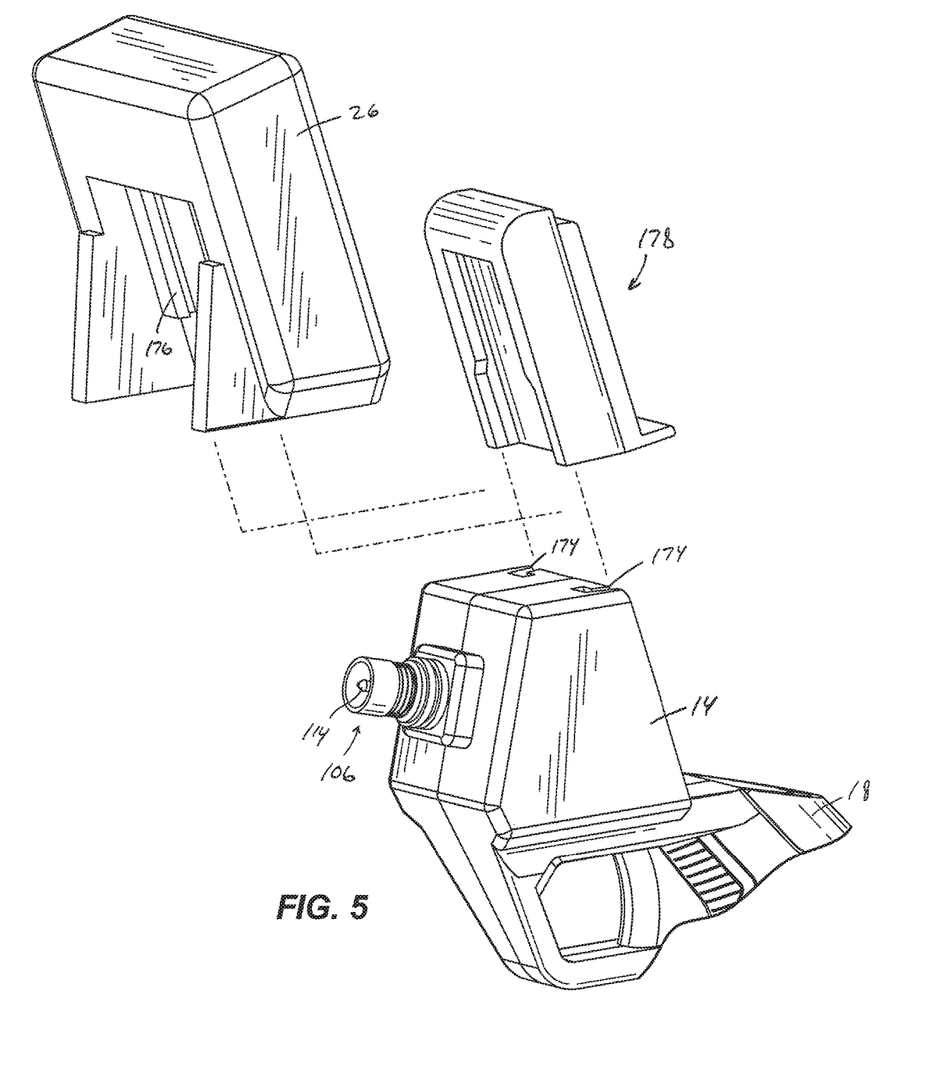
FIG. 5 is an exploded, rear perspective view of the visual inspection device of FIG. 1 with an intermediate module coupling the housing to a display unit.

With reference to FIG. 5, the display unit 26 is removably coupled to the housing 14 to allow a user to hold the display unit 26 separately from the remainder of the visual inspection device 10 during use. As such, the user may hold the display unit 26 steady, or place the display unit 26 on a stationary support surface, while maneuvering the remainder of the visual inspection device 10 during an inspection. In the illustrated embodiment of the device 10, the display unit 26 is slidably coupled to the housing 14 using a tongue and groove arrangement, with the housing 14 including parallel grooves 174 in which respective tongues or ribs 176 on the display unit 26 are slidably received. Alternatively, the display unit 26 may be removably coupled to the housing 14 using any of a number of different physical connections.

The visual inspection device 10 includes a wireless transmitter (e.g., a frequency modulated radio transmitter) positioned in the housing 14 for transmitting the image from either the camera unit 22 or the thermal imager unit 134 and a corresponding wireless receiver positioned in the display unit 26 for viewing the image on the screen 30. Although not shown, the visual inspection device 10 includes corresponding electrical contacts on the housing 14 and the display unit 26 that are engaged when the display unit 26 is attached to the housing 14 such that transmission of the image from either the camera unit 22 or the thermal imager unit 134 to the display unit 26 occurs through the electrical contacts. In operation of the visual inspection device 10, when the display unit 26 is detached from the housing 14, the wireless transmitter and receiver are automatically activated to provide a seamless transition from transmitting the image through the engaged electrical contacts to transmitting the image wirelessly using the wireless transmitter and receiver. Likewise, when the display unit 26 is re-attached to the housing 14, the wireless transmitter and receiver are automatically deactivated to provide a seamless transition back to transmitting the image through the engaged electrical contacts.

With continued reference to FIG. 5, the visual inspection device 10 may also include a module 178 selectively interconnecting the display unit 26 and the housing 14 and another wireless transmitter positioned in the module 178 for transmitting the image from either the camera unit 22 or the thermal imager unit 134 to a mobile electronic device (e.g., a smart phone, a tablet, etc.). As such, the image viewed by either the camera unit 22 or the thermal imager unit 134 can be remotely viewed by others using their mobile electronic devices, thereby enabling multiple users to view the same image that the operator of the visual inspection device 10 sees on the screen 30. The wireless transmitter in the module 178 may be a short-wavelength radio transmitter using Wi-Fi technology. Alternatively, other transmitters (e.g., a BLUETOOTH transmitter) may be utilized.

Although not shown, the module 178 includes pass-through electrical contacts that electrically interconnect the respective electrical contacts on the housing 14 and the display unit 26 when the module 178 interconnects the housing 14 and the display unit 26. The wireless transmitter in the module 178 also receives the image from the engaged electrical contacts on the housing 14 and the pass-through electrical contacts on the module 178. The module 178 may be utilized for transmitting the image to remote users' mobile devices, regardless of whether the display unit 26 is attached to the module 178.

With reference to FIG. 7, the flexible cable 34 includes an articulating section 212 for articulating or adjusting the position of the camera 46 relative to the remainder of the cable 34. The articulating section 212 includes spaced discs 216 interconnected by parallel coil springs 220. As such, the coil springs 220 maintain the discs 216 in a biased, linear orientation in which the articulating section 212 of the cable 34 is substantially coaxial with the camera 46. Lengths of the continuous wire 66 are disposed within respective sheaths 228 for protecting the lengths of wire 66 between the articulating section 212 and the mount 94.

With continued reference to FIG. 7, respective lengths of the wire 66, routed through the sheaths 228, are spiral-wound around a plurality of electrical wires 232 leading to the camera 46. A distal end of the sheaths 228 terminates in a first 216*a* of the discs 216, while respective lengths of the wire 66 are routed through apertures 236 in the individual discs 216, with the respective ends 70, 82 of the wire 66 being attached to the camera 46 in the manner described above. The sheaths 228 and corresponding lengths of wire 66 are twisted or spiral-wound around the electrical wires 232 along the length of the flexible cable 34, excluding the articulating section 212, to prevent pre-tensioning the wire 66 when the flexible cable 34 is adjusted or manipulated by the user. Accordingly, adjusting the flexible cable 34 does not impart any unwanted movement to the articulating section 212 or the camera 46.

In operation of the remote inspection device 10 with the articulating camera unit 22, the user may grasp and manipulate the flexible cable 34 to position the camera 46, and may also actuate the wire 66 to turn the camera 46 and obtain an additional degree of freedom. Particularly, by tensioning one length of the wire 66, the coil springs 220 bend and the individual discs 216 in the articulating section 212 skew to thereby turn the camera 46 in a first direction (FIG. 8). Likewise, by tensioning the other length of the wire 66, the coil springs 220 bend and the individual discs 216 in the articulating section 212 skew to thereby turn the camera 46 in an opposite, second direction (shown in phantom in FIG. 8). The lengths of wire 66 are tensioned by rotating the dial 62 in the manner described above.

Figure 9:
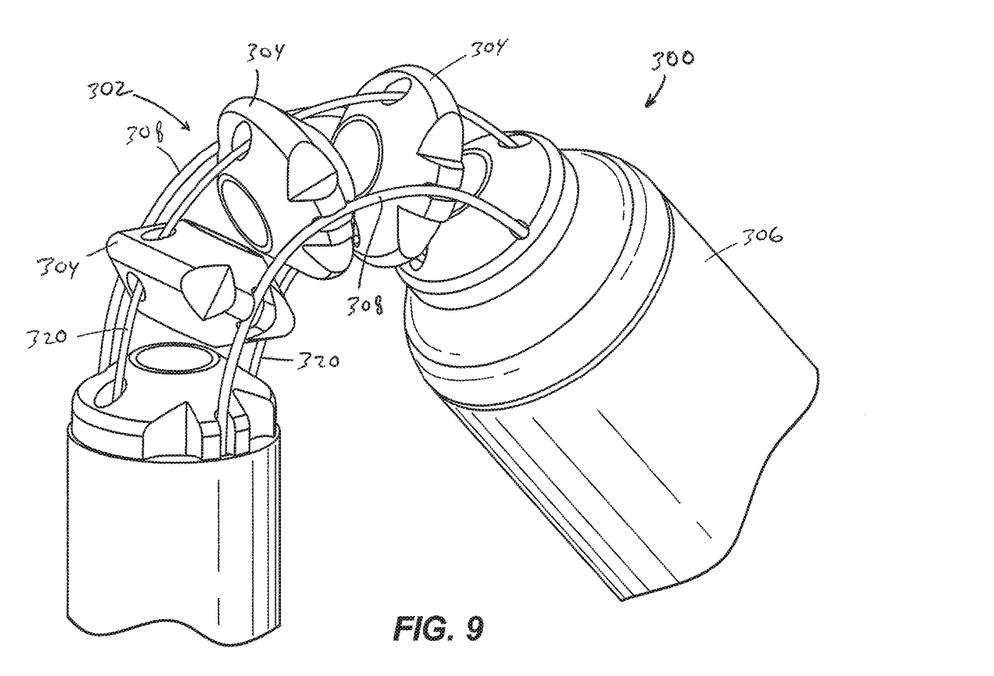
FIG. 9 is an enlarged, perspective view of another articulating section incorporated in an articulating camera unit for use with the visual inspection device of FIG. 1.
Figure 10:
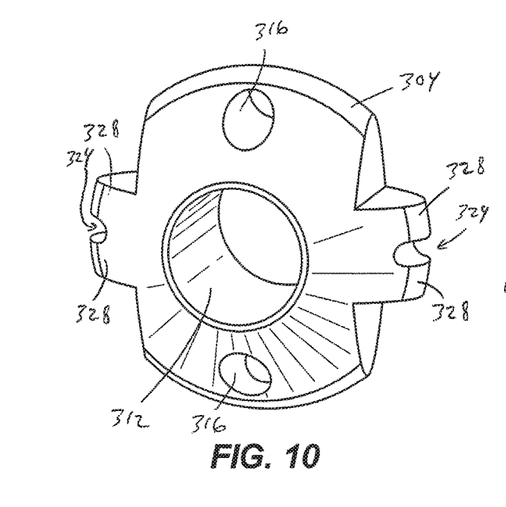
FIG. 10 is a front perspective view of a disc of the articulating section shown in FIG. 9.

FIG. 9 illustrates another articulating camera unit 300 for use with the visual inspection device 10 of FIG. 1. The articulating camera unit 300 includes an articulating section 302 having a series of spaced discs 304 interconnected by parallel resilient cables 308 (e.g., high-strand count stainless steel cable) that behave as springs for biasing the discs 304 in a linear orientation in which the articulating section 302 is substantially coaxial with a camera 306. With reference to FIG. 10, the discs 304 include a center aperture 312 for electrical wires (e.g., wires 232; FIG. 7) to pass through, and two apertures 316 for respective lengths of a continuous wire 320 to pass through (FIG. 9). In addition, each of the discs 304 includes two slots 324 (FIG. 10) formed within respective tabs 328 on opposite sides of the disc 304, and the resilient cables 308 are received within the slots 324 (FIG. 9). The resilient cables 308 are positioned within the slots 324 and the tabs 328 are crimped to mechanically deform the slots 324, thereby securing the resilient cables 308 to each of the discs 304. The articulating camera unit 300 operates in an identical manner as the unit 22 described above and shown in FIGS. 1-8.

Figure 11:
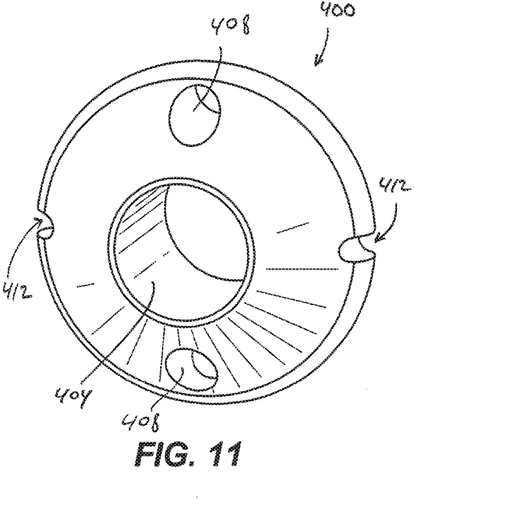
FIG. 11 is a front perspective view of another disc for use in the articulating section of FIG. 9.

FIG. 11 illustrates an alternative construction of a disc 400 for use in the articulating camera unit 300 of FIG. 9. The disc 400 includes a center aperture 404 for electrical wires (e.g., wires 232; FIG. 7) to pass through, and two apertures 408 (FIG. 11) for respective lengths of the continuous wire 320 to pass through, similar to the disc 304. In addition, the disc 400 includes two slots 412 formed on opposite sides of the disc 400 in which the resilient cables 308 are received. The resilient cables 308 are welded (i.e., electrically welded) or soldered to the disc 400 to interconnect a plurality of the discs 400. The disc 400 can be made of different materials. For example, for electrically welding the resilient cables 308 to the disc 400, the disc 400 may be made from stainless steel, and for soldering the resilient cables 308 to the disc 400 (e.g., using silver solder), the disc 400 may be made from brass or stainless steel.

Various features of the invention are set forth in the following claims.

What is claimed is:

1. A visual inspection device comprising:
   a housing;
   a handle coupled to the housing that is grasped by a user while the device is in use;
   an articulating camera unit coupled to the housing and including
      a flexible cable including a first end coupled to the housing and a second end,
      a camera coupled to the second end of the flexible cable and operable to transmit image data through the flexible cable,
      an articulation mechanism operable to articulate the camera relative to the flexible cable, the articulation mechanism includes a mount that is removably coupled to the housing, and
      a means for securing the mount to the housing in a plurality of different orientations relative to the housing; and
   a display unit coupled to the housing to display an image transmitted by the articulating camera unit;
   wherein the means for securing is a quick-release latch mechanism including a pivotable arm having a distal end that is received within a groove formed in an electrical connector extending from the housing for alternately securing the mount to the housing in each of the different orientations.

2. The visual inspection device of claim 1, wherein the articulation mechanism includes an actuator coupled to the housing, and wherein the actuator is manipulatable to articulate the camera relative to the flexible cable.

3. The visual inspection device of claim 2, further comprising:
   a boss having a square cross-sectional shape coupled to one of the housing and the mount; and
   a receptacle having a corresponding square cross-sectional shape defined by the other of the housing and the mount, wherein the boss is received within the receptacle in four different orientations to alternately position the actuator in each of the different orientations relative to the housing.

4. The visual inspection device of claim 3, wherein the articulation mechanism includes a continuous wire at least partially disposed within the flexible cable, wherein a first end of the wire is attached to the camera at a first location radially offset from a longitudinal axis of the camera, and wherein a second end of the wire is attached to the camera at a second location radially offset from the longitudinal axis of the camera.

5. The visual inspection device of claim 4, wherein the first and second locations are on opposite sides of the longitudinal axis.

6. The visual inspection device of claim 4, wherein a middle portion of the wire is coupled to the actuator, and wherein tension is developed in the wire proximate one of the first and second ends in response to movement of the actuator.

7. The visual inspection device of claim 6, wherein the actuator is a dial, and wherein the middle portion of the wire is wrapped around the dial such that rotation of the dial in a first direction develops tension in the wire proximate the first end, and rotation of the dial in a second direction develops tension in the wire proximate the second end.

8. The visual inspection device of claim 7, wherein the articulation mechanism further includes a pulley positioned between the dial and the flexible cable, and wherein the pulley is engaged with the wire for guiding the wire between the dial and the flexible cable.

9. The visual inspection device of claim 2, wherein the actuator is a dial that is rotatably coupled to the housing.

10. The visual inspection device of claim 9, wherein the dial is rotatable in a first direction for articulating the camera in a first direction relative to the flexible cable, and wherein the dial is rotatable in a second direction for articulating the camera in a second direction relative to the flexible cable.

11. The visual inspection device of claim 1, further comprising:
   a first electrical connector extending from the housing; and
   a second electrical connector extending from the first end of the flexible cable, the mount at least partially surrounding the second electrical connector.

12. The visual inspection device of claim 11, wherein the first electrical connector is one of a multi-conductor, cylindrical jack and a cylindrical socket, and wherein the second electrical connector is the other of the jack and the socket.

13. The visual inspection device of claim 12, further comprising:
   a boss having a square cross-sectional shape coupled to one of the housing and the mount; and a receptacle having a corresponding square cross-sectional shape defined by the other of the housing and the mount, wherein the boss is received within the receptacle in four different orientations to alternately position the actuator in each of the different orientations relative to the housing.

14. The visual inspection device of claim 13, wherein the articulation mechanism includes an actuator coupled to the housing, and wherein the actuator is manipulatable to articulate the camera relative to the flexible cable.

15. The visual inspection device of claim 1, wherein the flexible cable includes an articulating section having a plurality of interconnected discs.

16. The visual inspection device of claim 15, wherein the articulating section of the flexible cable includes a biasing member interconnecting the discs and biasing the discs to a linear orientation.

17. The visual inspection device of claim 16, wherein the biasing member is one of a coil spring and a cable.

18. The visual inspection device of claim 15, wherein the discs are one of crimped, welded, and soldered to the biasing member.

* * * * *